(12) United States Patent
Huynh

(10) Patent No.: US 8,978,574 B2
(45) Date of Patent: Mar. 17, 2015

(54) WATER DETECTING LABEL

(75) Inventor: Dieu Dai Huynh, Courcouronnes (FR)

(73) Assignee: Avery Dennison Corporation, Glendale, CA (US)

( * ) Notice: Subject to any disclaimer, the term of this patent is extended or adjusted under 35 U.S.C. 154(b) by 651 days.

(21) Appl. No.: 12/997,392

(22) PCT Filed: Jun. 10, 2009

(86) PCT No.: PCT/US2009/046829
§ 371 (c)(1),
(2), (4) Date: Jan. 31, 2011

(87) PCT Pub. No.: WO2009/152203
PCT Pub. Date: Dec. 17, 2009

(65) Prior Publication Data
US 2012/0067270 A1  Mar. 22, 2012

Related U.S. Application Data

(60) Provisional application No. 61/060,886, filed on Jun. 12, 2008.

(51) Int. Cl.
*G01N 31/22* (2006.01)

(52) U.S. Cl.
CPC .................................. *G01N 31/222* (2013.01)
USPC ......................................................... 116/206

(58) Field of Classification Search
USPC ............................ 116/206; 73/73; 283/96, 97
See application file for complete search history.

(56) References Cited

U.S. PATENT DOCUMENTS

| | | | | |
|---|---|---|---|---|
| 3,311,084 | A | * | 3/1967 | Edenbaum .................... 116/207 |
| 3,523,011 | A | * | 8/1970 | Bhiwandker et al. ......... 422/426 |
| 5,238,623 | A | * | 8/1993 | Mrozinski ....................... 264/48 |
| 5,660,925 | A | * | 8/1997 | Cooley et al. .............. 428/304.4 |
| 6,117,530 | A | * | 9/2000 | Jonza et al. .................... 428/212 |
| 7,081,286 | B2 | * | 7/2006 | Benim et al. ................. 428/35.3 |
| 7,105,225 | B2 | * | 9/2006 | Birkholz et al. .............. 428/354 |
| 7,892,639 | B2 | * | 2/2011 | Mess et al. .................... 428/354 |
| 2002/0061595 | A1 | * | 5/2002 | Yabuki et al. ................... 436/39 |
| 2005/0118415 | A1 | * | 6/2005 | LaBrosse et al. ............. 428/349 |
| 2007/0048480 | A1 | * | 3/2007 | Lavosky ..................... 428/40.1 |
| 2008/0145611 | A1 | * | 6/2008 | Mess et al. .................... 428/143 |

FOREIGN PATENT DOCUMENTS

| | | | | | |
|---|---|---|---|---|---|
| JP | 2008268332 | A | * | 11/2008 | ................ G09F 3/02 |
| WO | WO 9823920 | A1 | * | 6/1998 | ................ G01D 3/08 |
| WO | WO 03031531 | A1 | * | 4/2003 | ............. G01N 31/22 |

* cited by examiner

*Primary Examiner* — R. A. Smith
(74) *Attorney, Agent, or Firm* — Avery Dennison Corporation

(57) ABSTRACT

A fluid detecting adhesive article that indicates when a substrate or device to which the adhesive article is applied has been submerged in a fluid, such as water. The adhesive article may be an adhesive tape, label or sheet.

19 Claims, 1 Drawing Sheet

WATER DETECTING LABEL

CROSS-REFERENCE TO RELATED APPLICATION

The present application is a 371 of International Application No. PCT/US2009/046829, which was published in English on Dec. 17, 2009, and claims the benefit of U.S. Provisional Patent Application No. 61/060,886 filed Jun. 12, 2008, both of which are incorporated herein by reference in their entireties.

TECHNICAL FIELD OF THE INVENTION

This invention relates to a label, and specifically to a label for indicating exposure to fluids. The label is particularly useful for detecting whether an object, such as a portable electronic device, has been submersed in water.

BACKGROUND OF THE INVENTION

The use of portable electronic devices, such as mobile phones, MP3 players, portable gaming devices, personal digital assistants, satellite radios, and the like, is widespread and ever increasing. The manufacturers of such devices and the warranty providers for the devices would like to be informed if a device returned for service or replacement has failed or is defective because the device has been in contact with or immersed in water or another fluid. Water contact indicating labels placed on the device or within the device casing have been provided. It is desirable that these labels do not falsely indicate immersion in fluid when the device has merely been subjected to high humidity conditions present in some working environments and in various regions of the world. It is also desirable to produce a low cost water detecting label.

SUMMARY OF THE INVENTION

The present invention is directed to a fluid detecting adhesive article that indicates when a substrate to which the adhesive article is applied has been submerged in a fluid, such as water. The adhesive article may be an adhesive tape, label or sheet.

The adhesive article, in one embodiment, comprises a fluid absorbent layer having a first major surface and a second major surface and a pressure sensitive adhesive layer underlying the second major surface of the absorbent layer. The absorbent layer, in one embodiment, is water absorbent. A transparent topcoat having a first major surface and a second major surface overlies the first major surface of the absorbent layer. The transparent topcoat provides humidity resistance to the absorbent layer. A color migrating layer is provided adjacent to the second major surface of the absorbent layer and overlying the adhesive layer. A release liner may be adhered to the adhesive layer.

DETAILED DESCRIPTION OF THE INVENTION

The term "overlies" and cognate terms such as overlying and the like, when referring to the relationship of one or a first layer relative to another or a second layer, refers to the fact that the first layer partially or completely overlies the second layer. The first layer overlying the second layer may or may not be in contact with the second layer. For example, one or more additional layers may be positioned between the first and the second layer. The term "underlies" and cognate terms such as "underlying" and the like have similar meanings except that the first layer partially or completely lies under, rather than over the second layer.

Figure 1:
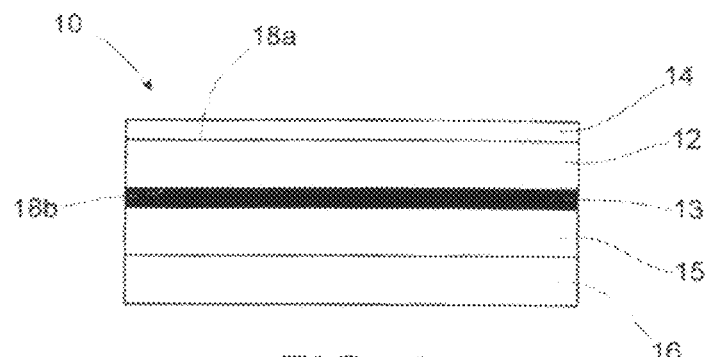
FIG. 1 is a cross-sectional view of an embodiment of a label of the present invention having a continuous color migrating layer.

An embodiment of the water detecting label is illustrated in FIG. 1. The label 10 includes absorbent layer 12 having a first major surface 18a and a major second surface 18b. The second major surface 18b of absorbent layer 12 overlies continuous color migrating layer 13. A transparent topcoat 14 overlies the first major surface 18a of absorbent layer 12. A pressure sensitive adhesive layer 15 underlies the second major surface 18b of absorbent layer 12 and is adhered to the color migrating layer 13. When the absorbent layer 12 becomes saturated, the pigmented material of the color migrating layer 13 migrates through the absorbent layer 12, and becomes visible through the transparent topcoat 14. The pigmented material that has migrated through the absorbent layer 12 remains visible after the absorbing material has dried. A removable release liner 16 may be adhered to the adhesive layer to protect the adhesive until use.

Figure 2:
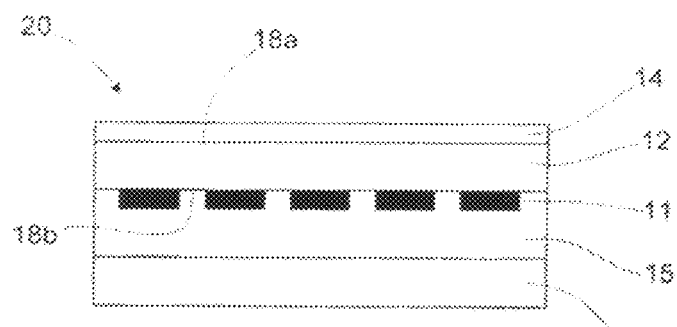
FIG. 2 is a cross-sectional view of an embodiment of a label of the present invention having a discontinuous color migrating layer.

The embodiment illustrated in FIG. 2 is substantially similar to that illustrated in FIG. 1, except color migrating layer 11 is discontinuous. The color migrating layer may be applied in a pattern to the second major surface of absorbent layer 12. The pattern may comprise lines, dots, circles, squares or any other geometric design, or may comprise one or more alpha numeric characters. The pattern may also be random.

Figure 3:
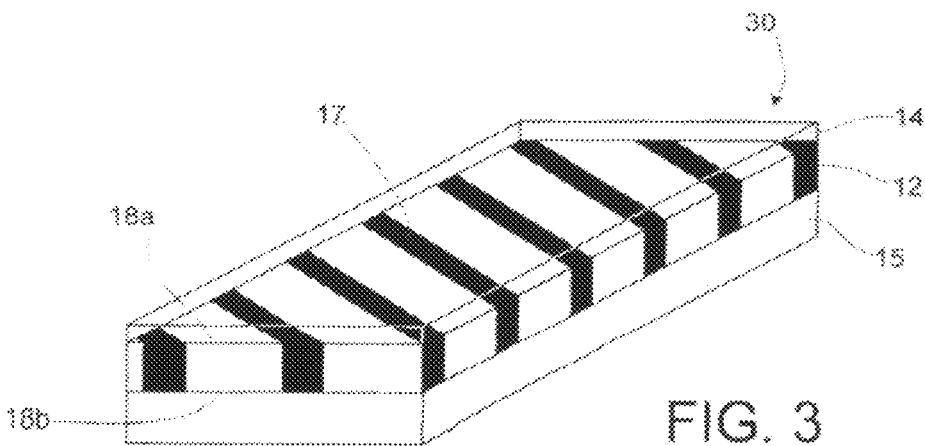
FIG. 3 is a perspective view of the label of FIG. 2 after exposure to fluid.

FIG. 3 illustrates the embodiment shown in FIG. 2 after the absorbent layer 12 has become saturated and the pigmented material 17 of the color migrating layer 11 has migrated through the absorbent layer 12. The pigmented material 17 is visible through the transparent topcoat 14 and remains visible even after the absorbent layer has dried.

Absorbent Layer

The absorbent layer will absorb fluid, yet it will not significantly deteriorate structurally when saturated with water or another fluid. Additionally, the absorbent layer will not become saturated under high humidity conditions. The absorbent layer may comprise a porous film, a fibrous film, a woven or non-woven fabric, a polyolefin film, a wood-based paper or a wood-free paper. Wood-free paper includes, for example, paper made from hemp, papyrus, cattails, rushes, bagasse, wheat straw, banana paper and cereal.

The absorbent layer may be transparent or opaque. Typically, the absorbent layer is opaque. In one embodiment, as the absorbent layer becomes saturated, it loses its opacity. In another embodiment, the absorbent layer remains opaque when saturated.

In one embodiment, the absorbent layer comprises a wood-free, uncoated paper having a basis weight of at least 60 gsm (g/m$^2$), or at least 70 gsm, or at least 80 gsm or at least 90 gsm. In one embodiment, the wood-free paper has a porosity of at least 800 ml/min. An example of a useful wood-free paper is that commercially available from UPM.

Topcoat

A transparent topcoat overlies the absorbent layer. The term "transparent" when referring to one or more layers of the label film means that any material beneath such layers can be seen through such layers. The transparent topcoat provides humidity protection to the underlying absorbent layer so that the absorbent layer does not become saturated when the label is subjected to humid conditions. Additionally, the transparent topcoat may be printable.

In one embodiment, the topcoat comprises an aqueous acrylic dispersion. An example of a useful commercially available aqueous acrylic dispersion is NeoCryl BT-36, an anionic, alkali solubilized acrylic from DSM NeoResins. The topcoat may also contain other conventional additives such as UV absorbers, anti-block agents and anti-static agents.

The topcoat layer can be prepared by applying the topcoat composition to the surface of the absorbent layer using a conventional coating or other application technique, and then drying the coating at room temperature or elevated temperature in an oven to remove the water. Non-limiting examples of coating techniques include slot die, air knife, brush, curtain, blade, floating knife, gravure, kiss roll, knife-over-blanket, knife-over-roll, offset gravure, reverse roll, reverse-smoothing roll, rod and squeeze roll coating. For label products, the topcoat composition can be applied to the absorbent layer using any conventional technique or process, including without limitation, coating "on press" during the converting process (e.g., in concert with the processes of die-cutting, matrix stripping, etc.), coating off-press using a separate coater, and other application methods.

In general, the dry coat weights of the topcoat may range from about 1 to about 10 or even 20 or more gsm (g/m$^2$). In other embodiments, the dry coat weight may range from about 1 to about 7 gsm, and in yet a further embodiment, the dry coat weight may range from about 1 to about 5.5 gsm.

The topcoat is a coating and not a film that may be adhesively laminated to or heat sealed onto the absorbing layer.

Color Migrating Layer

The color migrating layer comprises a continuous or patterned layer of a pigmented material that migrates into the absorbing layer when the absorbing layer becomes saturated. The pigmented material is then visible, through the transparent topcoat, on the outermost surface of the absorbing layer. When the substrate dries, the pigmented material remains visible on the outermost surface of the absorbing layer.

In one embodiment, the color migrating layer is coated onto the absorbing layer. In another embodiment, the color migrating layer is coated onto the adhesive layer, which is then adhered to the absorbing layer.

In one embodiment, the color migrating layer comprises a water soluble ink coated onto the substrate. Examples of water soluble inks include those typically used in ink jet printing. In general, water soluble inks include one or more water soluble dyes, water, at least one wetting agent and at least one surfactant. An example of a useful color migrating layer comprises a color changing ink primer coating available as 12-901348-8 from Siegwerk. The color changing ink primer as initially applied is black in color, but as it contacts the fluid of the saturated absorbent layer and migrates through the absorbent layer, it becomes red in color.

The color migrating layer may be applied to the absorbing layer by conventional coating or printing techniques including ink jet, flexographic, gravure, offset, digital or letter press printing.

Adhesive

A description of useful pressure sensitive adhesives may be found in Encyclopedia of Polymer Science and Engineering, Vol. 13, Wiley-Interscience Publishers (New York, 1988). Additional description of useful PSAs may be found in Polymer Science and Technology, Vol. 1, Interscience Publishers (New York, 1964). Conventional PSAs, including acrylic-based PSAs, rubber-based PSAs and silicone-based PSAs are useful. The PSA may be a solvent based or may be a water based adhesive. In one embodiment, the PSA comprises an acrylic emulsion adhesive.

In one embodiment, the adhesive may be formed from an acrylic based polymer. It is contemplated that any acrylic based polymer capable of forming an adhesive layer with sufficient tack to adhere to a substrate may function in the present invention. In certain embodiments, the acrylic polymers for the pressure-sensitive adhesive layers include those formed from polymerization of at least one alkyl acrylate monomer containing from about 4 to about 12 carbon atoms in the alkyl group, and present in an amount from about 35-95% by weight of the polymer or copolymer, as disclosed in U.S. Pat. No. 5,264,532. Optionally, the acrylic based pressure-sensitive adhesive might be formed from a single polymeric species.

The glass transition temperature of a PSA layer comprising acrylic polymers can be varied by adjusting the amount of polar, or "hard monomers", in the copolymer, as taught by U.S. Pat. No. 5,264,532, incorporated herein by reference. The greater the percentage by weight of hard monomers is an acrylic copolymer, the higher the glass transition temperature. Hard monomers contemplated useful for the present invention include vinyl esters, carboxylic acids, and methacrylates, in concentrations by weight ranging from about zero to about thirty-five percent by weight of the polymer.

The PSA can be acrylic based such as those taught in U.S. Pat. No. 5,164,444 (acrylic emulsion), U.S. Pat. No. 5,623, 011 (tackified acrylic emulsion) and U.S. Pat. No. 6,306,982. The adhesive can also be rubber-based such as those taught in U.S. Pat. No. 5,705,551 (rubber hot melt). It can also be radiation curable mixture of monomers with initiators and other ingredients such as those taught in U.S. Pat. No. 5,232, 958 (UV cured acrylic) and U.S. Pat. No. 5,232,958 (EB cured). The disclosures of these patents as they relate to acrylic adhesives are hereby incorporated by reference.

Another useful acrylic PSA comprises a blend of emulsion polymer particles with dispersion tackifier particles as generally described in Example 2 of U.S. Pat. No. 6,306,982. The polymer is made by emulsion polymerization of 2-ethylhexyl acrylate, vinyl acetate, dioctyl maleate, and acrylic and methacrylic comonomers as described in U.S. Pat. No. 5,164,444 resulting in the latex particle size of about 0.2 microns in weight average diameters and a gel content of about 60%. In one embodiment, the adhesive is an acrylic adhesive commercially available as AE3349 from Avery Dennison.

In addition to the tackifiers, other additives may be included in the PSAs to impart desired properties. For example, plasticizers may be included, and they are known to decrease the glass transition temperature of an adhesive composition containing elastomeric polymers. Antioxidants also may be included on the adhesive compositions. Cutting agents such as waxes and surfactants also may be included in the adhesives. Light stabilizers, heat stabilizers, and UV absorbers also may be included in the adhesive compositions. Ultraviolet absorbers include benzotriazol derivatives, hydroxy benzyl phenones, esters of benzoic acids, oxalic acid, diamides, etc. Light stabilizers include hindered amine light stabilizers, and the heat stabilizers include dithiocarbamate compositions such as zinc dibutyl dithiocarbamate.

The adhesive layer may be a single layer or comprise multiple layers of adhesive. The multiple layers of adhesive may be applied to the absorbent layer simultaneously using methods known in the art.

Liner

The release liners that may be utilized in the adhesive article constructions of the present invention can consist of any of a variety of materials known to those of skill in the art to be suitable as release liners. In one embodiment, the release liner comprises a 90# stayflat liner. Other suitable release liners include silicone coated films or polycoated kraft, as are known in the art. Suitable pre-siliconized release liners are available commercially. In one embodiment, the release liner comprises a glassine white 60# liner.

The water detecting label of the present invention will change color when submerged in water, yet is capable of withstanding high humidity, i.e., 50° C., 95% RH for 5 days, without changing color. In one embodiment, the water detecting label is capable of withstanding condensation, i.e., −25° C. for 1 hour, immediately followed by 80° C., 95% RH for 30 minutes, without changing color.

While the invention has been explained in relation to its preferred embodiments, it is to be understood that various modifications thereof will become apparent to those skilled in the art upon reading the specification. Therefore, it is to be under stood that the invention disclosed herein is intended to cover such modifications as fall within the scope of the appended claims.

What is claimed is:

1. A water detecting adhesive article comprising:
   a fluid absorbent layer having a first major surface and a second major surface;
   a pressure sensitive adhesive layer underlying the second major surface of the absorbent layer;
   a dried transparent topcoat applied to the first major surface of the fluid absorbent layer in the form of an aqueous acrylic dispersion, the transparent topcoat having a first major surface and a second major surface, the second major surface overlying the first major surface of the absorbent layer; and
   a discontinuous color migrating layer adjacent to the second major surface of the absorbent layer and overlying the adhesive layer.

2. The adhesive article of claim 1 wherein the fluid absorbent layer has a porosity of at least about 800 ml/min.

3. The adhesive article of claim 1 wherein the absorbent layer is water absorbent.

4. The adhesive article of claim 1 wherein the fluid absorbent layer comprises wood-free paper.

5. The adhesive article of claim 4 wherein the wood-free paper is made from hemp, papyrus, cattails, rushes, bagasse, wheat straw, banana paper, or cereal.

6. The adhesive article of claim 1 wherein the adhesive layer comprises an emulsion acrylic adhesive.

7. The adhesive article of claim 1 wherein the coat weight of the topcoat is about 1 gsm to about 20 gsm.

8. The adhesive article of claim 6 wherein the coat weight of the topcoat is about 1 gsm to about 10 gsm.

9. The adhesive article of claim 1 wherein the color migrating layer comprises a pattern.

10. The adhesive article of claim 1 wherein the color migrating layer comprises at least one alpha numeric character.

11. The adhesive article of claim 1 wherein the color migrating layer comprises a water soluble ink.

12. The adhesive article of claim 1 further comprising a release liner adhered to the adhesive layer.

13. The adhesive article of claim 1 wherein the first major surface of the transparent topcoat is printable.

14. The adhesive article of claim 1 wherein the absorbent layer is transparent.

15. A water detecting adhesive article comprising:
   a fluid absorbent layer having a first major surface and a second major surface;
   a pressure sensitive adhesive layer underlying the second major surface of the absorbent layer;
   a transparent topcoat having a first major surface and a second major surface, the second major surface overlying the first major surface of the absorbent layer wherein the transparent topcoat comprises an aqueous acrylic dispersion; and
   a color migrating layer adjacent to the second major surface of the absorbent layer and overlying the adhesive layer;
   wherein the transparent topcoat is a dried transparent topcoat applied to the first major surface of the fluid absorbent layer in the form of an aqueous acrylic dispersion.

16. The adhesive article of claim 15 wherein the coat weight of the topcoat is about 1 gsm to about 20 gsm.

17. The adhesive article of claim 15 wherein the coat weight of the topcoat is about 1 gsm to about 10 gsm.

18. The adhesive article of claim 15 wherein the absorbent layer is transparent.

19. A water detecting adhesive article comprising:
   a fluid absorbent layer having a first major surface and a second major surface;
   a pressure sensitive adhesive layer underlying the second major surface of the absorbent layer;
   a transparent topcoat having a first major surface and a second major surface, the second major surface overlying the first major surface of the absorbent layer; and
   a discontinuous color migrating layer adjacent to the second major surface of the absorbent layer and embedded into the adhesive layer,
   wherein the transparent topcoat is a dried transparent topcoat applied to the first major surface of the fluid absorbent layer in the form of an aqueous acrylic dispersion.

* * * * *